United States Patent [19]

Hess et al.

[11] Patent Number: 5,713,929

[45] Date of Patent: Feb. 3, 1998

[54] ARRHYTHMIA AND FIBRILLATION PREVENTION PACEMAKER USING RATCHET UP AND DECAY MODES OF OPERATION

[75] Inventors: Michael F. Hess; Michael R. S. Hill, both of Minneapolis; John T. Meador, Half Moon Bay, all of Minn.; R. Hardwin Mead, Palo Alto, Calif.

[73] Assignee: Medtronic, Inc., Minneapolis, Minn.

[21] Appl. No.: 642,717

[22] Filed: May 3, 1996

[51] Int. Cl.⁶ .................. A61N 1/362; A61N 1/39
[52] U.S. Cl. .................. 607/14; 607/15; 607/4
[58] Field of Search .................. 607/14, 15, 5, 607/9, 4

[56] References Cited

U.S. PATENT DOCUMENTS

| | | | |
|---|---|---|---|
| 3,857,399 | 12/1974 | Zacouto | 607/9 |
| 4,030,510 | 6/1977 | Bowers | 607/9 |
| 4,163,451 | 8/1979 | Lesnick et al. | 607/14 |
| 4,556,063 | 12/1985 | Thompson | 607/32 |
| 4,830,006 | 5/1989 | Haluska et al. | 607/14 |
| 4,917,115 | 4/1990 | Flammang | 607/19 |
| 5,127,404 | 7/1992 | Wybomy | 607/32 |
| 5,284,491 | 2/1994 | Sutton | 607/17 |
| 5,292,339 | 3/1994 | Stephens et al. | 607/15 |
| 5,350,409 | 9/1994 | Stoop | 607/17 |
| 5,395,397 | 3/1995 | Lindgren | 607/14 |
| 5,400,796 | 3/1995 | Wecke | 128/705 |
| 5,411,524 | 5/1995 | Rahul | 607/4 |
| 5,480,413 | 1/1996 | Greenhut et al. | 607/14 |
| 5,584,867 | 12/1996 | Limousin et al. | 607/14 |
| 5,632,267 | 5/1997 | Högnelid et al. | 607/5 |

OTHER PUBLICATIONS

McDonald et al., "Permanent Pacing as Treatment for Hypertrophic Cardiomyopathy", *Am. J. Cardiol.* 68(1):108–110 Jul. 1991.

Barold. S., "Cardiac Pacing In Special and Complex Situations", *Cardiac Pacing*, vol. 10, No. 4, (1992) pp. 573–591.

Murgatroyd et al., "A New Pacing Algorithm for the Suppression of Atrial Fibrillation", *PACE*, vol. 17 *NASPE Abstracts Apr.* 1994 *part II.*

Clark et al., "Propranolol Induced Bradycardia in Tetralogy of Fallot", *Br. Heart J.*, 1989 61:378–9.

Ishikawa, et al., "Preventive Effects of Pacemakers on Paroxysmal Atrial Fibrillation in Patients with Bradycardia–Tachcardia Syndrome", *AF Prevention by Pacing in SSS*, 22 Aug. 1994 p. 175.

*Primary Examiner*—Marvin M. Lateef
*Assistant Examiner*—Carl H. Layno
*Attorney, Agent, or Firm*—Harold R. Patton; Michael B. Atlass

[57] ABSTRACT

New pacing algorithm defines faster than indicated pacing rate during detection of PAC's/PVC's and reduces rate after awhile to a safety rate unless natural depolarizations are detected.

47 Claims, 15 Drawing Sheets

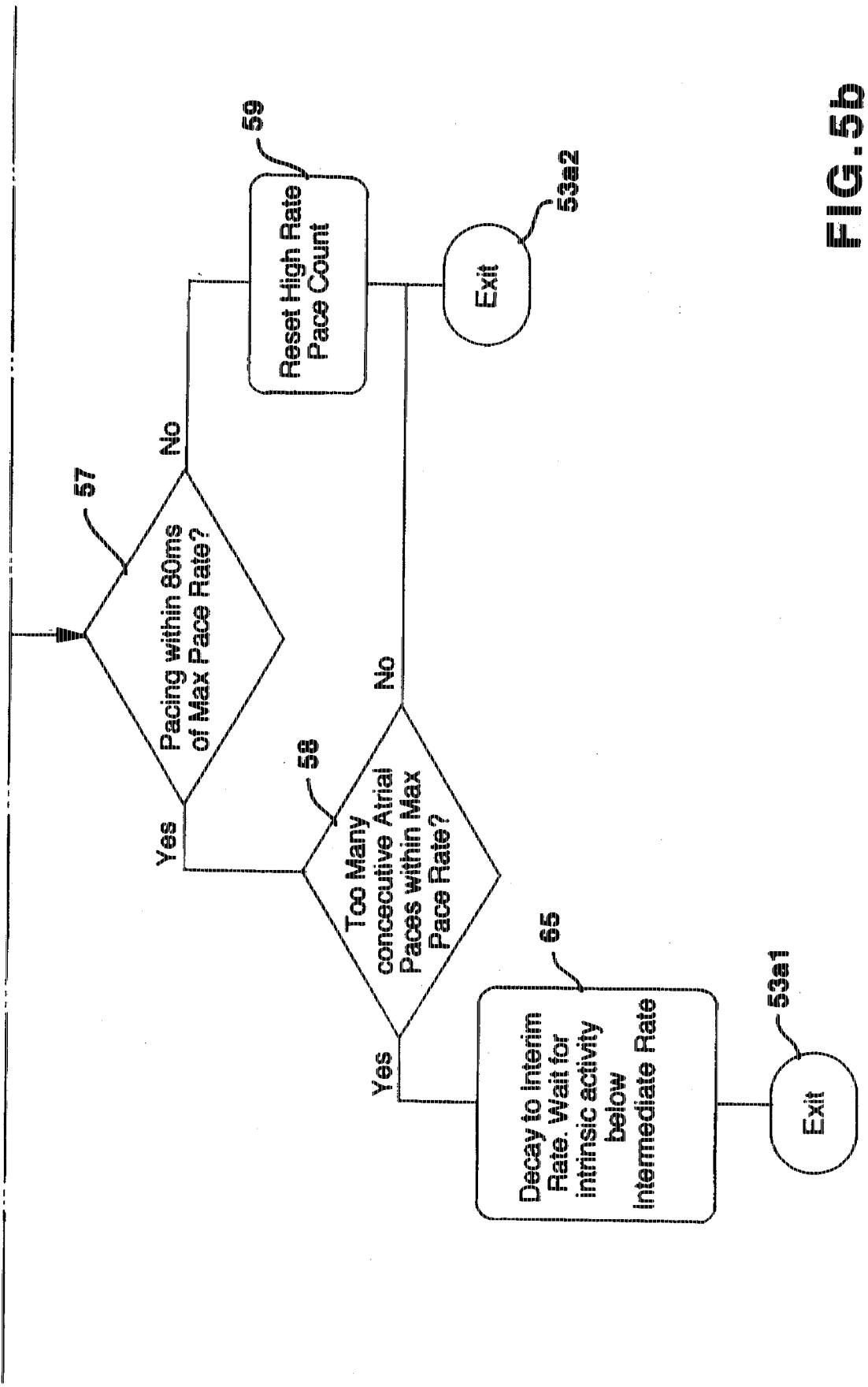

| FIG.6a | FIG.6b |
|---|---|
| FIG.6c | FIG.6d |
| FIG.6e | FIG.6f |

FIG.6

ARRHYTHMIA AND FIBRILLATION PREVENTION PACEMAKER USING RATCHET UP AND DECAY MODES OF OPERATION

This invention relates to the field of pacemakers and their timing algorithms and processes and has particular application to modification of atrial pacing to preferably avoid atrial fibrillation and atrial tachycardia. In addition, this therapy can be applied to suppression of ventricular arrhythmias such as ventricular tachycardia or ventricular fibrillation through the application of this teaching to ventricular and/or atrial pacing.

BACKGROUND

Pacing literature has pointed out that pacing may be effectiveness in stabilizing otherwise unstable atria, for example "cardiac pacing in special and complex situations" Cardiology Clinics, 10:4 pp. 573–91, 1992 (Barold, SS). See also Br Heart J., 115: page 478, 1988 (Clark M., Sutton R. Ward D. et al.) and "A new pacing algorithm for suppression of atrial fibrillation (Murgatroyd F., et al.) in PACE 17, Part II, page 863.

Modifying pacing rate or pacing intervals for various purposes has been shown in the past also. See for example in defining the AV escape interval applied to HOCM pacing as in "Permanent Pacing as Treatment for Hypertropic CardioMyopathy" by McDonald et al., Am. J. of Cardiology, V. 68, pp. 108–110, July. Hysteresis has been provided so that the pacer may turn itself off in the presence of naturally conducted depolarizations. For this later category see for example Bowers (U.S. Pat. No. 4,030,510) and Sutton (U.S. Pat. No. 5,284,491) and others.

Doctors have recently begun to recognize that dual chamber pacemakers by themselves seem to reduce the presence of AT's and AF's. See Ishikawa et al., "Preventative Effects of Pacemakers on Paroxysmal Atrial Fibrillation in Patients with Bradycardia-Tachycardia Syndrome". (published in the journal, "Artificial Organs", 1994).

Nevertheless, to date no one has provided a pacemaker that purposefully overdrives the atrium at a rate faster than the indicated natural rate or sensor rate. Prior to the introduction of such a device it has been felt that countervailing criteria were more important. For example allowing the heart to pace at its natural rate, or driving the heart to a predetermined rate corresponding to an activity level were and still are considered to primary pacing objectives. It was also widely recognized that any more than the minimum necessary pacing pulses reduce the useful life of a pulse generator because each pulse takes more power from the battery. Because of these contraindications, such a device has never previously been provided.

SUMMARY OF THE INVENTION

Figure 1:
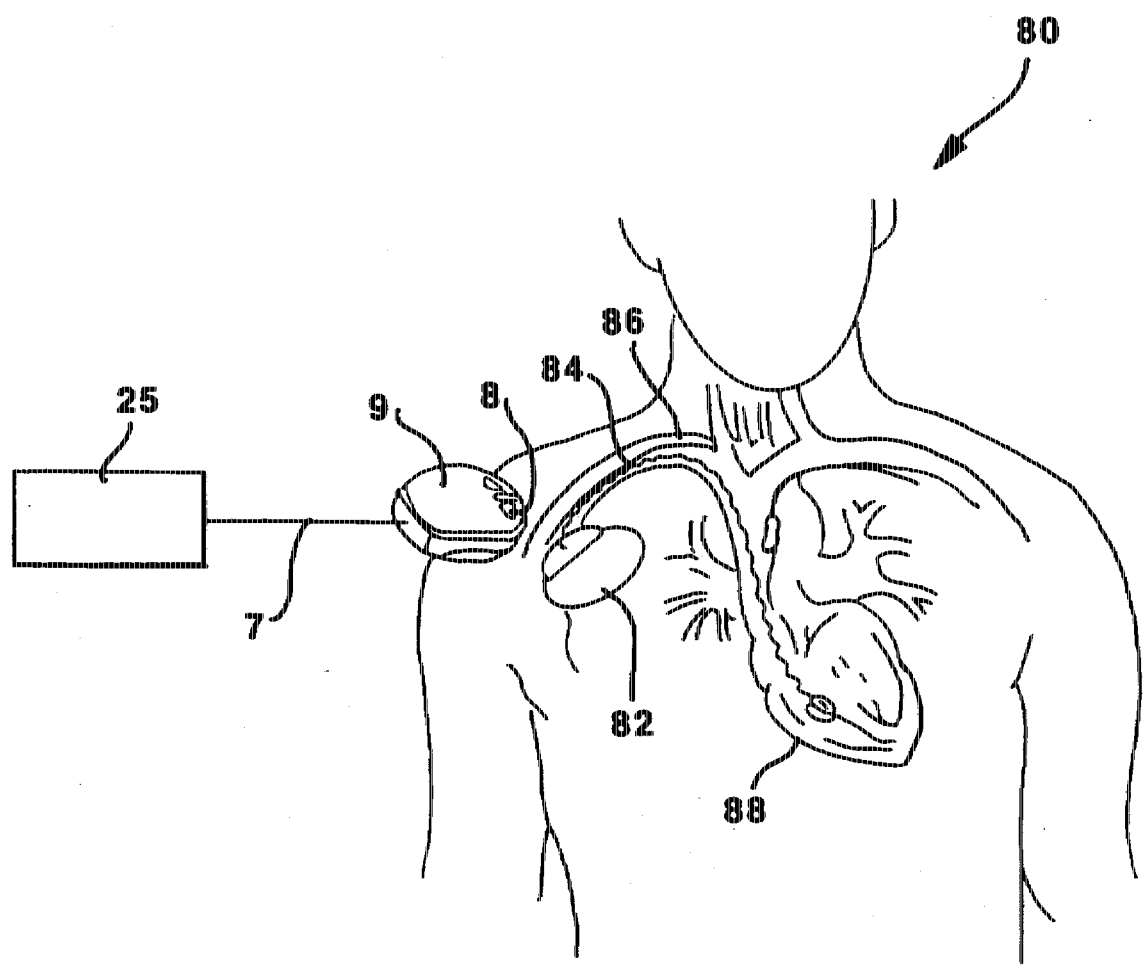
FIG. 1 is a diagram of a human with a pacer and a programmer for communication therewith.

Provided here is a process and apparatus for controlling a heart pacemaker comprising means for pacing at a rate which is just above what usual indications might otherwise suggest is the best pacing rate. This has particular application to pacing at just above the sinus rate since the first implementation of this invention is designed to eliminate or attenuate the amount of atrial tachycardia and atrial fibrillation. Other indications for what the sinus rate should be include sensor rate which is generated by an activity sensor or based on other means such as minute ventilation, etc. It should be recognized that it is contrary to the usual application of this invention to pace above a sensor rate if the sinus rate is less than the sensor rate. In such situations the preferred embodiment simply paces at the sensor rate. In general, the "just above the usual rate" is a rate determined by periodically or at predetermined times reducing the pacing rate until a natural rhythm of heart beats is found in the atrium, (i.e., sinus node generated atrial depolarizations) and then increasing the paced rate again by a second predetermined amount. This second mount is designed to eliminate the presence AF and AT (also called Atrial Fibrillation and Atrial Tachycardia).

The feature provided by this invention can be enabled or disabled. When enabled it will start by decreasing the atrial escape interval on consecutive beats until atrial pacing is established. After a programmable number of beats, the escape interval will be increased incrementally until intrinsic atrial activity is once again discovered. (This is called a "decay" phase.)

When atrial intrinsic depolarizations are sensed, then the escape interval will be again decreased in increments until consistent atrial pacing is restored. (This is called a "capture" or "ratchet up" phase).

Some additional features include using a lower pulse width and/or amplitude for the pacing pulses during the decay phase than during the capture phase; not using atrial refractory events in atrial interval calculations used for setting the escape interval; and employing the mechanism for preventing long term atrial pacing at a maximum rate to avoid CHF conditions.

We presently believe that because a higher frequency of the occurrence of arrhythmias correspond to a dispersion of refractoriness, and because heart repolarization patterns tend to mimic the pattern of depolarization that the method and apparatus taught here is theoretically sound. In other words because consistent atrial (or dual chamber) pacing as taught herein will achieve a more consistent pattern of depolarization, the corresponding patterns of repolarization will also be consistent and the frequency of arrhythmias should decrease, perhaps because of the minimized temporal and spatial dispersion of refractoriness.

Further, application of the algorithms for controlling the pacemaker taught here can be made to drive the pacing pulses driven to the ventricles, and thus provide consistent ventricular pacing, with or without consistent atrial pacing as described herein.

PREFERRED EMBODIMENT OF THE INVENTION

In FIG. 1 a human body 80 is fitted with an implanted medical device 82, in this example, a hermetically sealed, biocompatable, implanted pulse generator or pacemaker. It is connected to the heart 88 by a lead 84 in the subclavien vein 86 as is a common practice at the current time for implanting pacemaker devices. The programmer head 9 with hand operated switches like 8 is preferably connected by a balanced transmission wire system or cable assembly 7 to a "Programmer" or computer that is used to program pulse generators and retains information from them. Such a device as a Programmer 25 may have a keyboard and display means for communication with an attendant (not shown). Such a system is used to communicate telemetrically with the implanted device 82.

Figure 2:
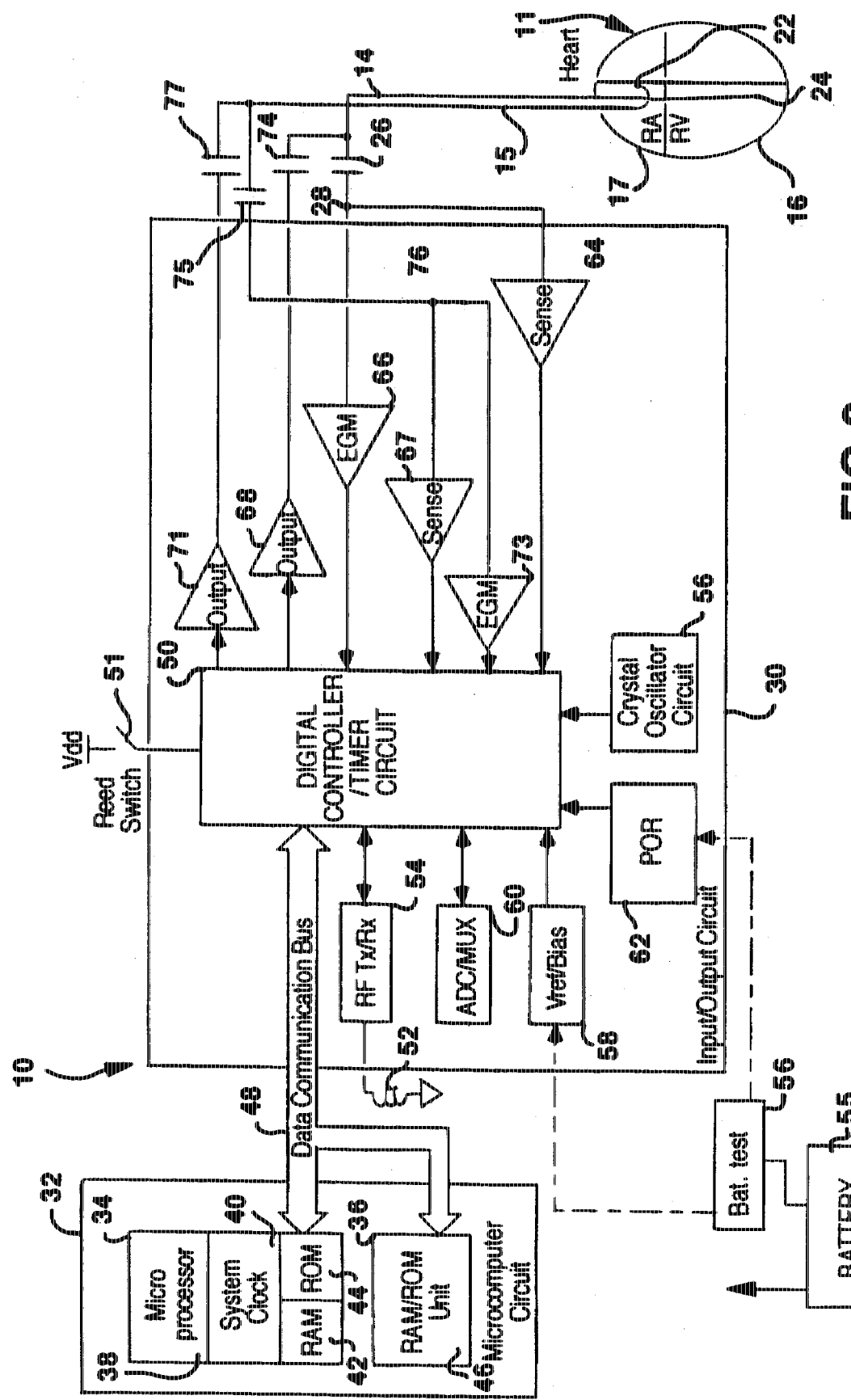
FIG. 2 is a block diagram of the component circuit parts and devices within a pacemaker and its association with the heart.

FIG. 2 is a block circuit diagram illustrating one possible form of a pacemaker 10 capable of carrying out the present invention. A detailed description of its general function follows.

Although the present invention is described in conjunction with a microprocessor-based architecture, it is understood that it could be implemented in other technology such as digital logic-based, custom integrated circuit (IC) architecture, analog circuits, etc., if desired.

Pacemakers that pace in the atrium often use two leads such as leads 14, 15. For this example embodiment other configurations could also be used as those of ordinary skill in the art will realize. Lead 14 includes an electrode 24 located near its distal end positioned within the right ventricle 16. Electrode 24 is coupled by a lead conductor 14 through an input capacitor 26 to the node 28, and to the input/output terminals of an input/output circuit 30. Lead 15 has a distal electrode positioned within the right atrium 17. Electrode 22 is coupled by a lead conductor 15 through an input capacitor 75 to a node 76, and to the input/output terminals of the Input/Output circuit 30.

Circuit 30 contains the operating input and output analog circuits for digital controlling and timing circuits to detect electrical signals derived from the heart, such as the cardiac electrogram (EGM or ECG). It may also receives output from sensors (not shown but which may be connected to the leads 14 and 15 or in the pacemaker body or connector block, etc.), and it is the part which applies stimulating pulses to the heart under the control of software-implemented algorithms in a Microcomputer Circuit 32.

Microcomputer Circuit 32 is often configured as an On-Board Circuit 34 and an Off-Board Circuit 36. On-Board Circuit 34 includes a microprocessor 38, a system clock 40, and on-board RAM 42 and ROM 44. Off-Board Circuit 36 includes an off-board RAM/ROM Unit 46. Microcomputer Circuit 32 is coupled by Data Communication Bus 48 to a Digital Controller/Timer Circuit 50. Microcomputer Circuit 32 may be fabricated of custom IC devices augmented by standard RAM/ROM components or fabricated in a chip on a hybrid circuit board.

It will be understood by those skilled in the art that the electrical components represented in FIG. 2 are powered in preferred embodiments by an appropriate implantable-grade battery power source 55. A battery test circuit 56 will provide information to the controller or the microcomputer directly, in most embodiments through a Vref value circuit like 58 or a suitably configured POR circuit containing end of life indicator or other battery life/power level circuits as are well known in the art.

An antenna 52 is connected to Input/Output Circuit 30 for purposes of uplink/downlink telemetry through a radio frequency (RF) Transmitter/Receiver Circuit (RF TX/RX) 54. Telemetering both analog and digital data between antenna 52 and an external device, such as an external "Programmer" (like the device at numeral 25 in FIG. 1) is accomplished in preferred embodiments by means such as are described in U.S. Pat. No. 5,127,404, "Telemetry Format for Implantable Medical Device", (incorporated herein by reference). Also in preferred embodiments, a reed switch 51 is connected to Input/Output Circuit 30 to enable patient follow-up by disabling sense amplifier 146 and enabling telemetry and programming functions, as is known in the art. Commonly a reed switch needs to be closed to telemeter out data but some devices will not contain reed switches, preferring to use other know devices or methods acceptable to guarantee reliability of telemetry data or initiation and against inappropriate usage.

A Crystal Oscillator Circuit 56, is preferred for providing the main timing clock signals to Digital Controller Timer Circuit 50. Most timing periods depend on a clock to turn on or off under program control, and the length of timing is generally established with reference to a number of clock cycles. A Vref/Bias Circuit 58 generates a stable voltage reference and bias currents for the analog circuits of Input/Output Circuit 30. An ADC/Multiplexer Circuit (ADC/MUX) 60 digitizes analog signals and voltages to provide telemetry and a replacement time-indicating or end-of-life function (EOL). A Power-on-Reset Circuit (POR) 62 functions to initialize the pacemaker 10 with programmed values during power-up, and reset the program values to default states upon the detection of a low battery condition or transiently in the presence of certain undesirable conditions such as unacceptably high electromagnetic or electrical interference (EMI), for example.

The operating commands for controlling the timing of the pacemaker depicted in FIG. 2 are coupled by bus 48 to Digital Controller/Timer Circuit 50 wherein digital timers set the overall escape interval of the pacemaker and may have separate atrial and ventricular escape intervals, as well as various refractory (PVARP), blanking (PVAB) and other timing windows for controlling the operation of the peripheral components within Input/Output Circuit 50. For this invention these may also include atrial interval values, AV intervals, and so forth.

Digital Controller/Timer Circuit 50 is coupled to sense amplifiers (SENSE) 64 and 67, and to electrogram (EGM) amplifiers 66 and 73 for receiving amplified and processed signals picked up from electrode 24 through lead 14 and capacitor 26, and for receiving amplified and processed signals picked up from electrode 22 through lead 15 and capacitor 75, representative of the electrical activity of the patient's ventricle 16 and atrium 17, respectively. Similarly, SENSE amplifiers 64 and 67 produce sense event signals for re-setting the escape interval timer within Circuit 50. The electrogram signal developed by EGM amplifier 66 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", incorporated herein by reference.

Output pulse generators 68 and 71 provide the pacing stimuli to the patient's heart 11 through output capacitors 74 and 77 and leads 14 and 15 in response to paced trigger signals developed by Digital Controller/Timer Circuit 50 each time the escape interval times out, or an externally transmitted pacing command has been received, or in response to other stored commands as is well known in the pacing art In a preferred embodiment of the present invention, pacemaker 10 is capable of operating in various non-rateresponsive modes which include DDD, DDI, VVI, VOO and VVT, as well as corresponding rate-responsive modes of DDDR, DDIR, VVIR, VOOR and VVTR as well as the A (atrial) analogs of these: AAI/R, AAT/R, AOO/R, et cetera. Further, pacemaker 10 can be programmably configured to operate such that it varies its rate only in response to one selected sensor output, or in response to both sensor outputs, if desired. Many other features and functions of pacemakers may be incorporated without going beyond the scope of this invention.

Figure 3:
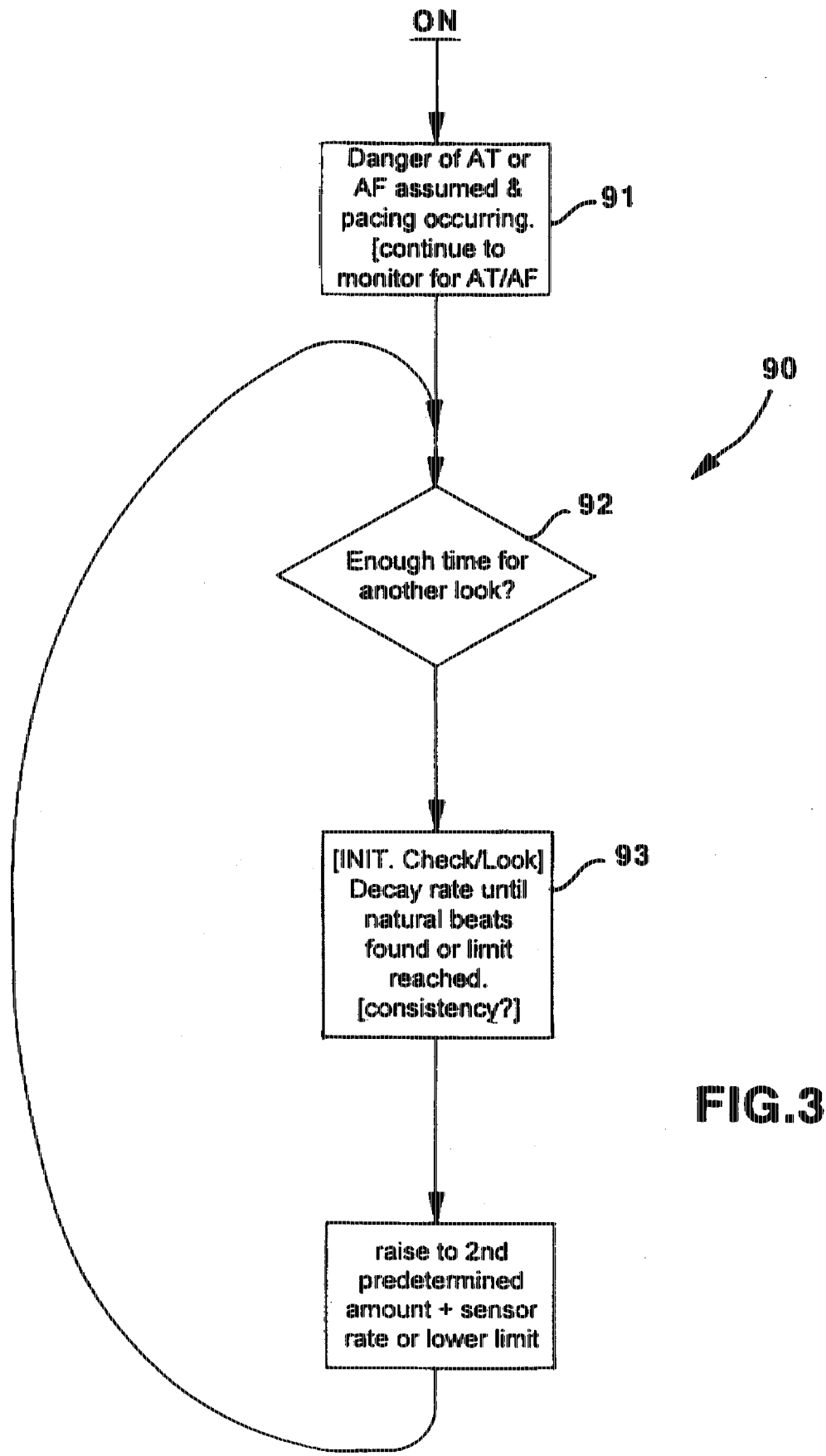
FIG. 3. is a basic process flow diagram in accord with the preferred embodiment of the invention.

Referring now to FIG. 3 in which a generalized flow chart is described with reference to chart 90, the first is a determination of whether or not this flow diagram will be employed determined in step 91 by either the doctor's concurrence or internal other algorithms (which are not described) that indicate the presence of paroxysmal or chronic AT or AF. Step 91 also checks to see that atrial pacing is enabled. A timer or flag is checked to see if enough time has gone by (as monitored with reference to the clock circuit of FIG. 2) in step 92 to decrease the atrial pacing rate in order to determine whether there was a natural sinus rhythm "just under" that pacing rate. In step 92, the rate is iteratively reduced (decayed) until a natural beat is sensed or a lower limit is reached.

At this time the algorithm can take one of several turns within step 93 such that it may either check for a natural sinus rate to determine what that is and boost the rate of pacing a conveniently safe amount above that or it can ratchet the rate upward until no naturally conductive beats are found. If the later branch is taken, a certain number of atrial paces in a row without natural conduction or premature natural conduction must occur for the algorithm to assume that an appropriate pacing rate has been reached.

Figure 4A:
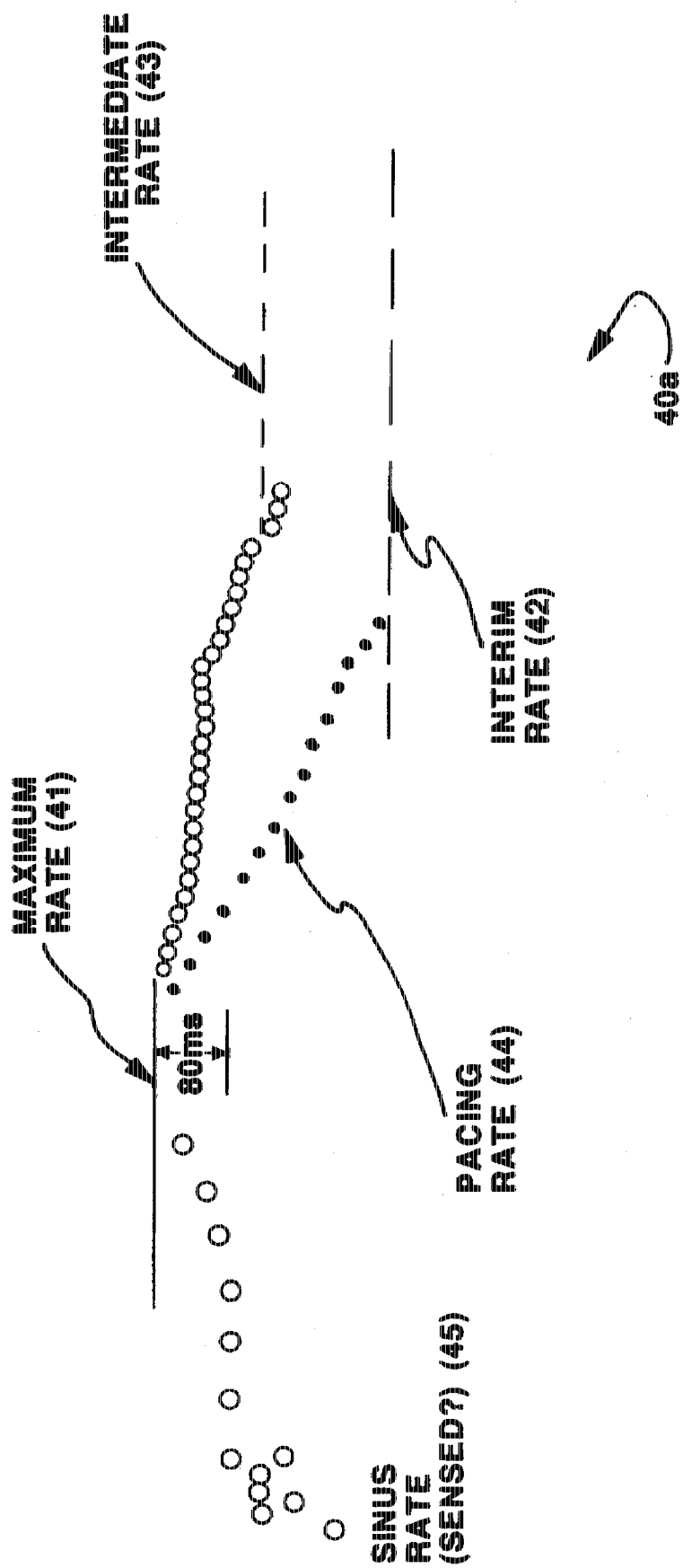
FIGS. 4a and 4b are graphs of activity of pacing and sinus beats illustrating various points in the flow charts.
Figure 4B:
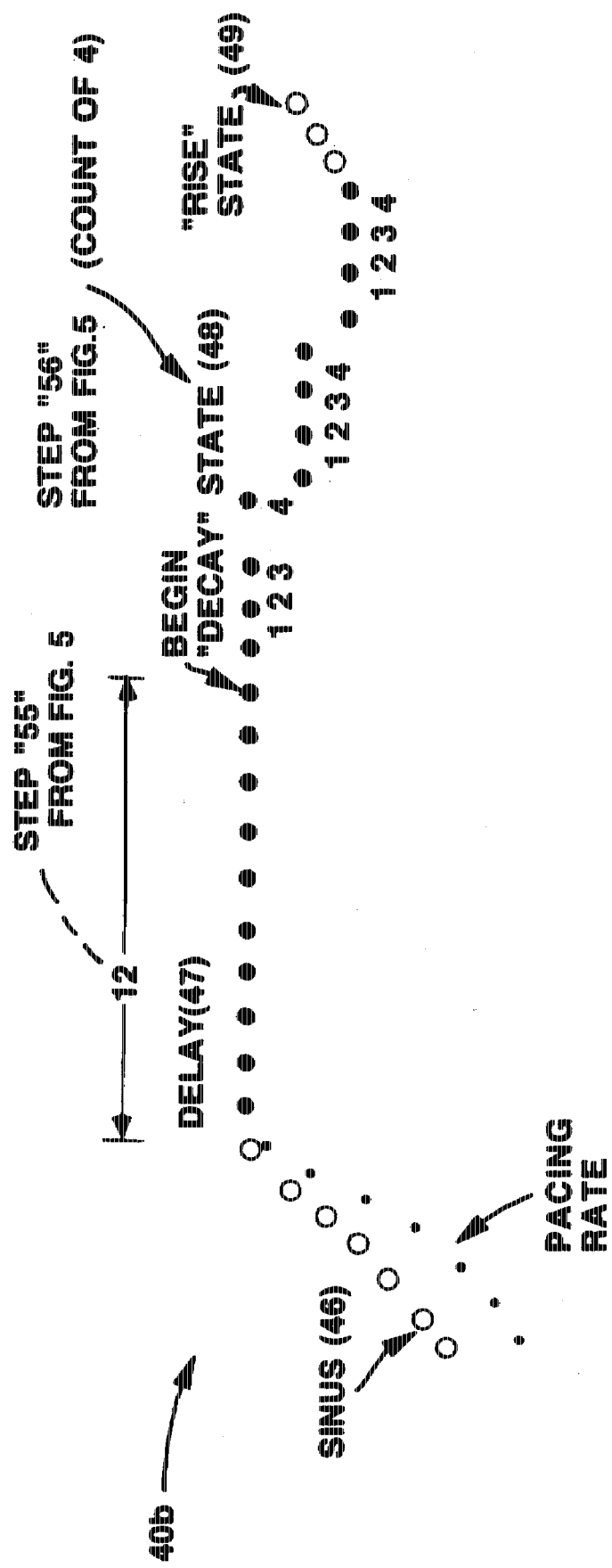
Figure 5A:
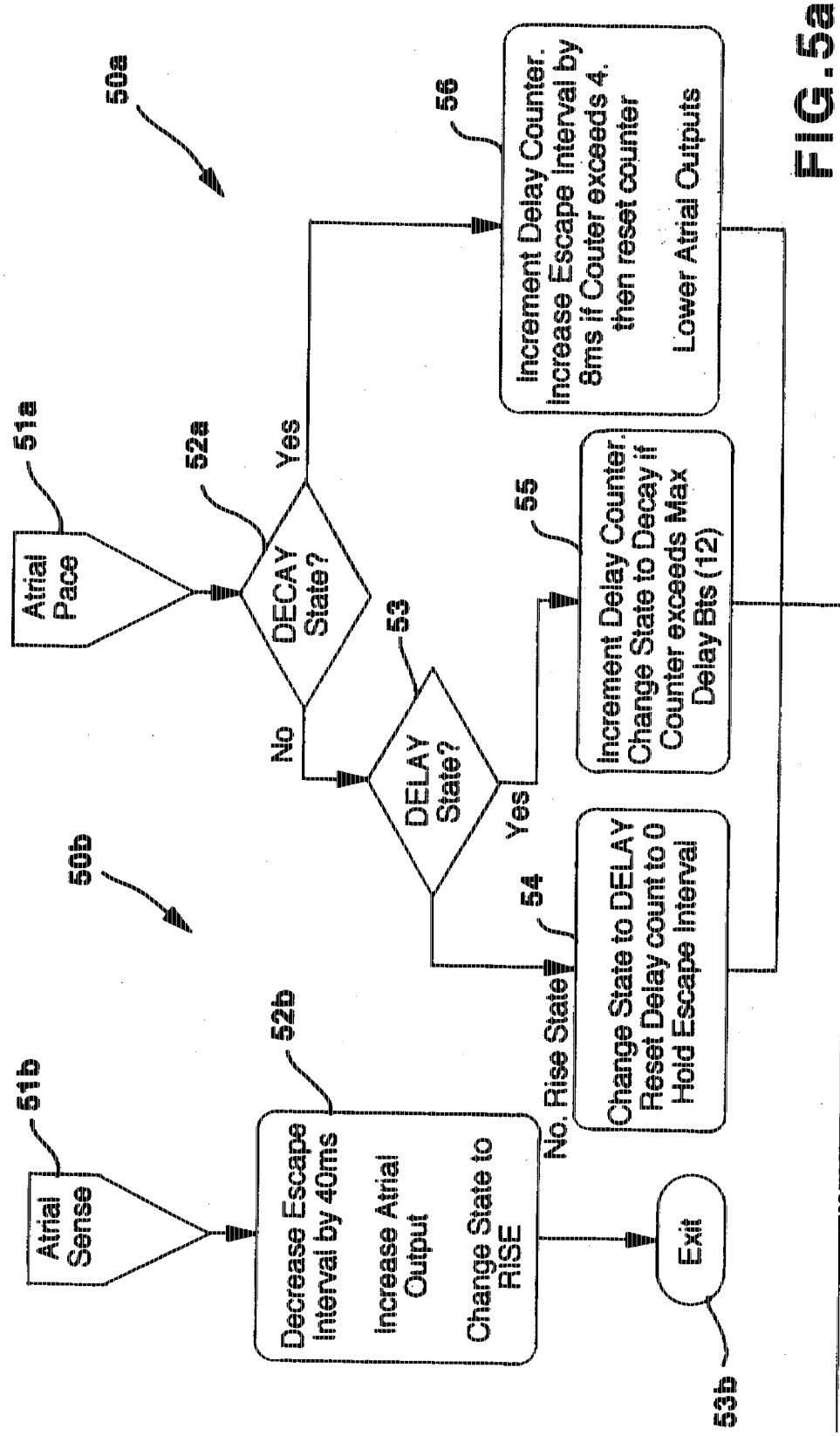
FIG. 5 is a flow diagram of an algorithm for implementation of the processes in accord with the preferred embodiment of this invention.
Figure 6A:
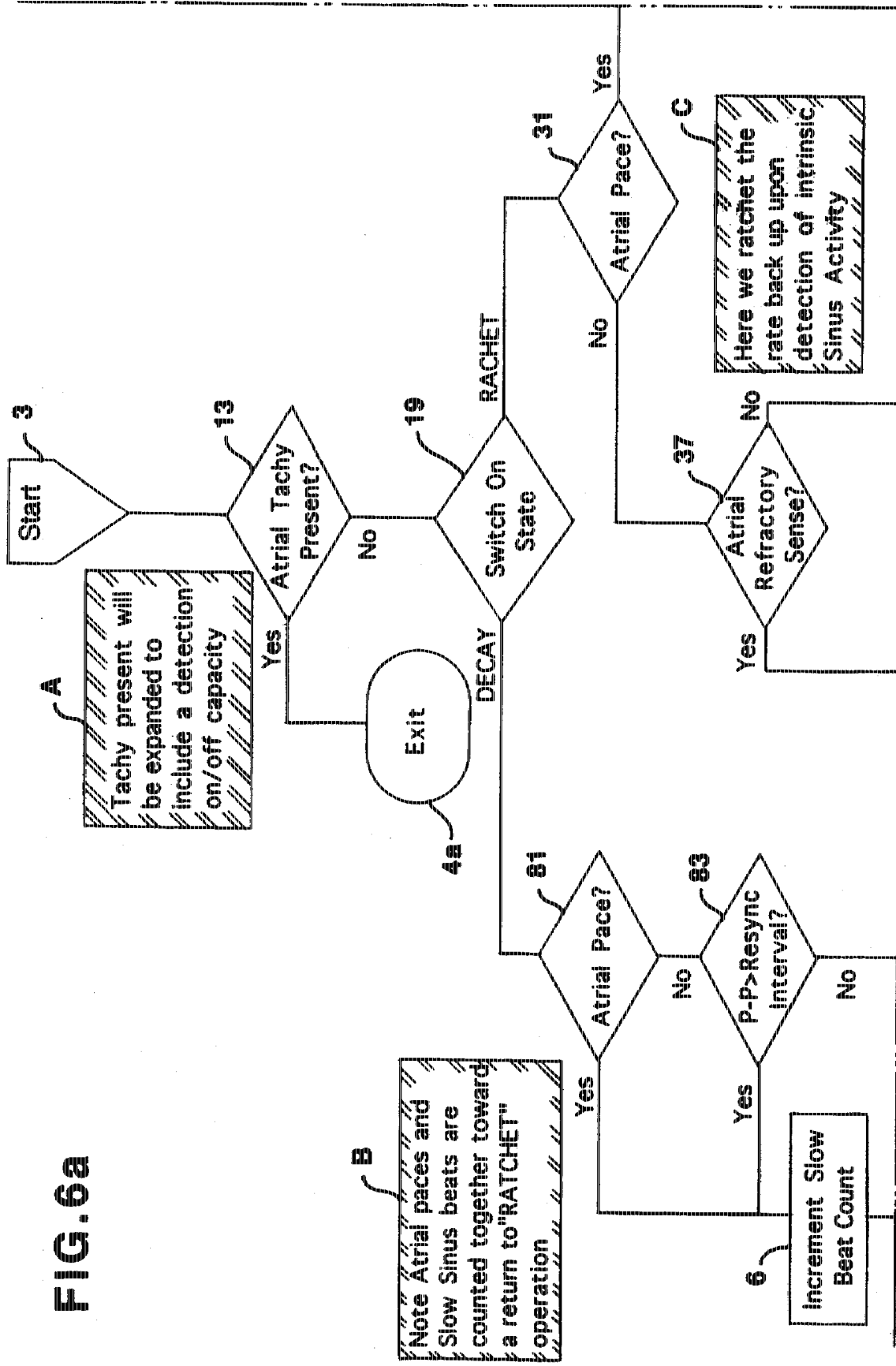
FIG. 6 is a flow diagram like FIG. 4 for a second algorithm in accord with a preferred embodiment of this invention.
Figure 6B:
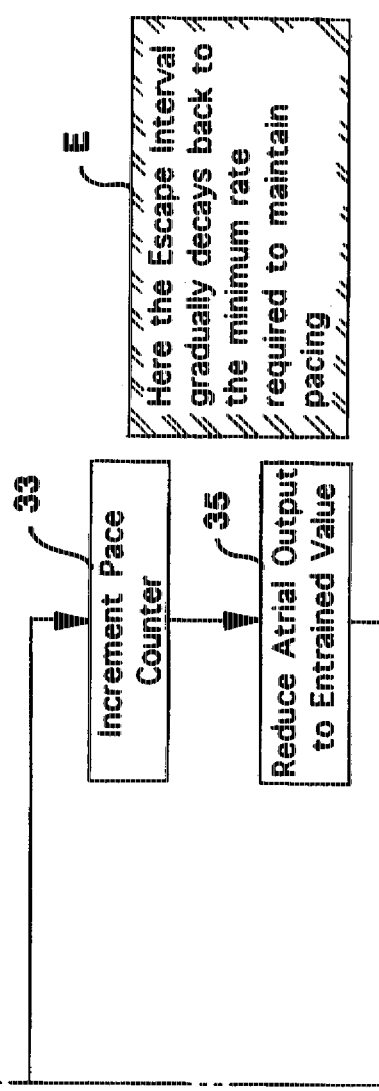
Figure 6C:
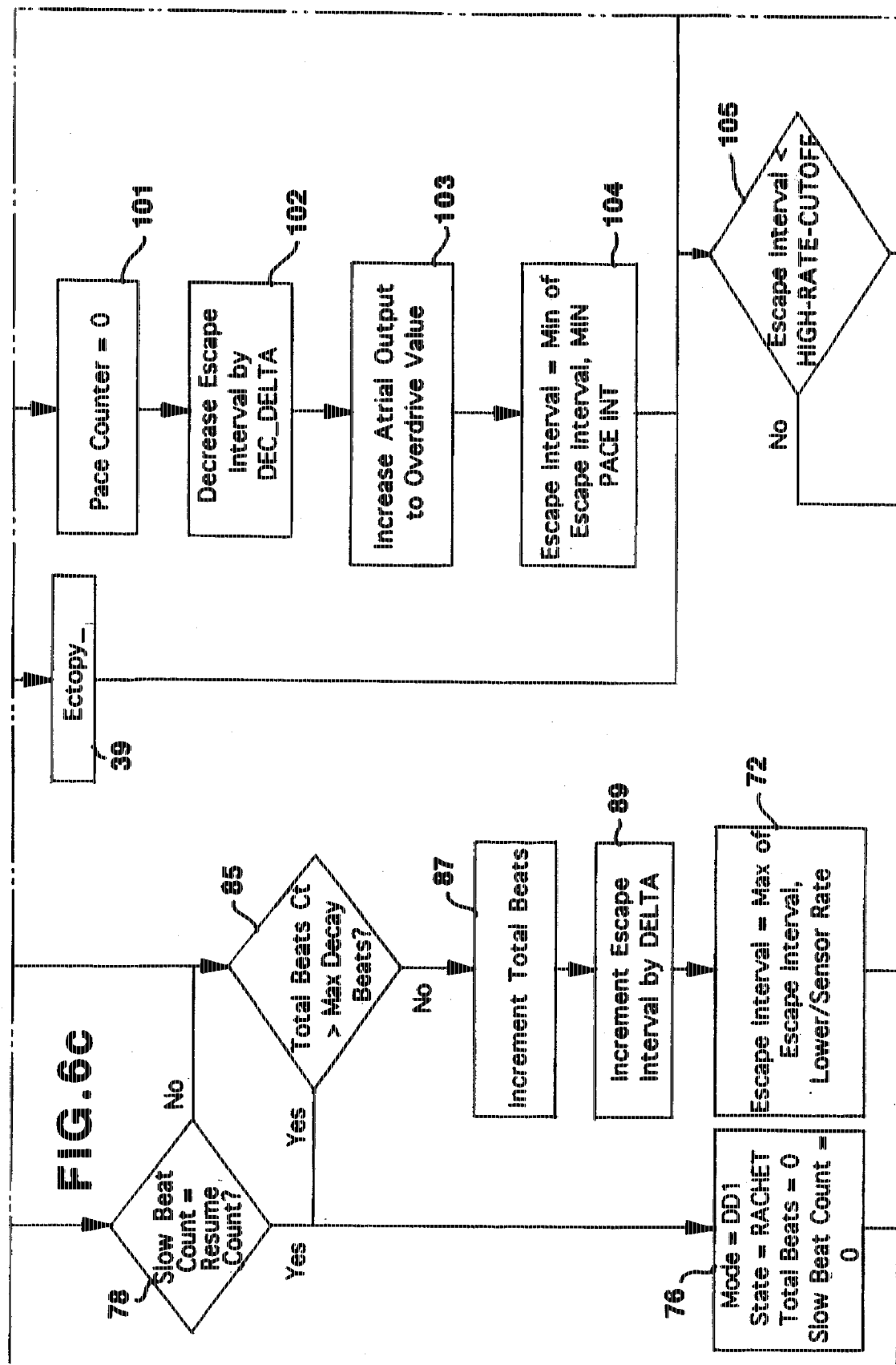
Figure 6D:
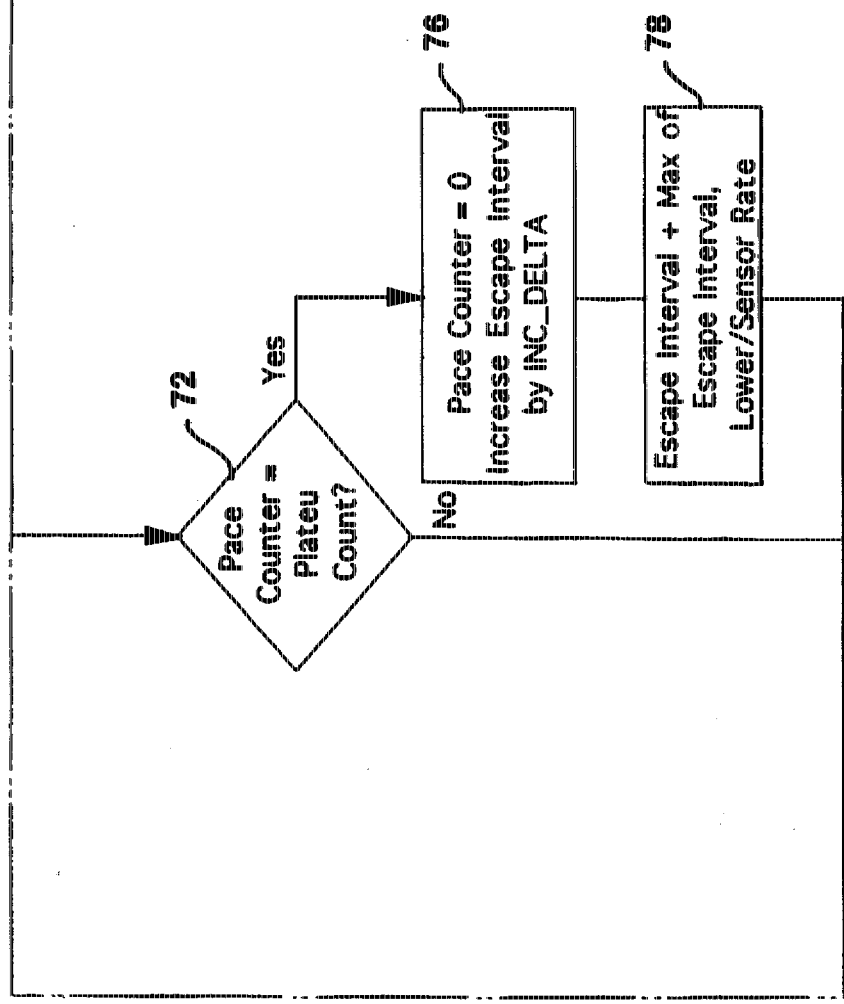
Figure 6E:
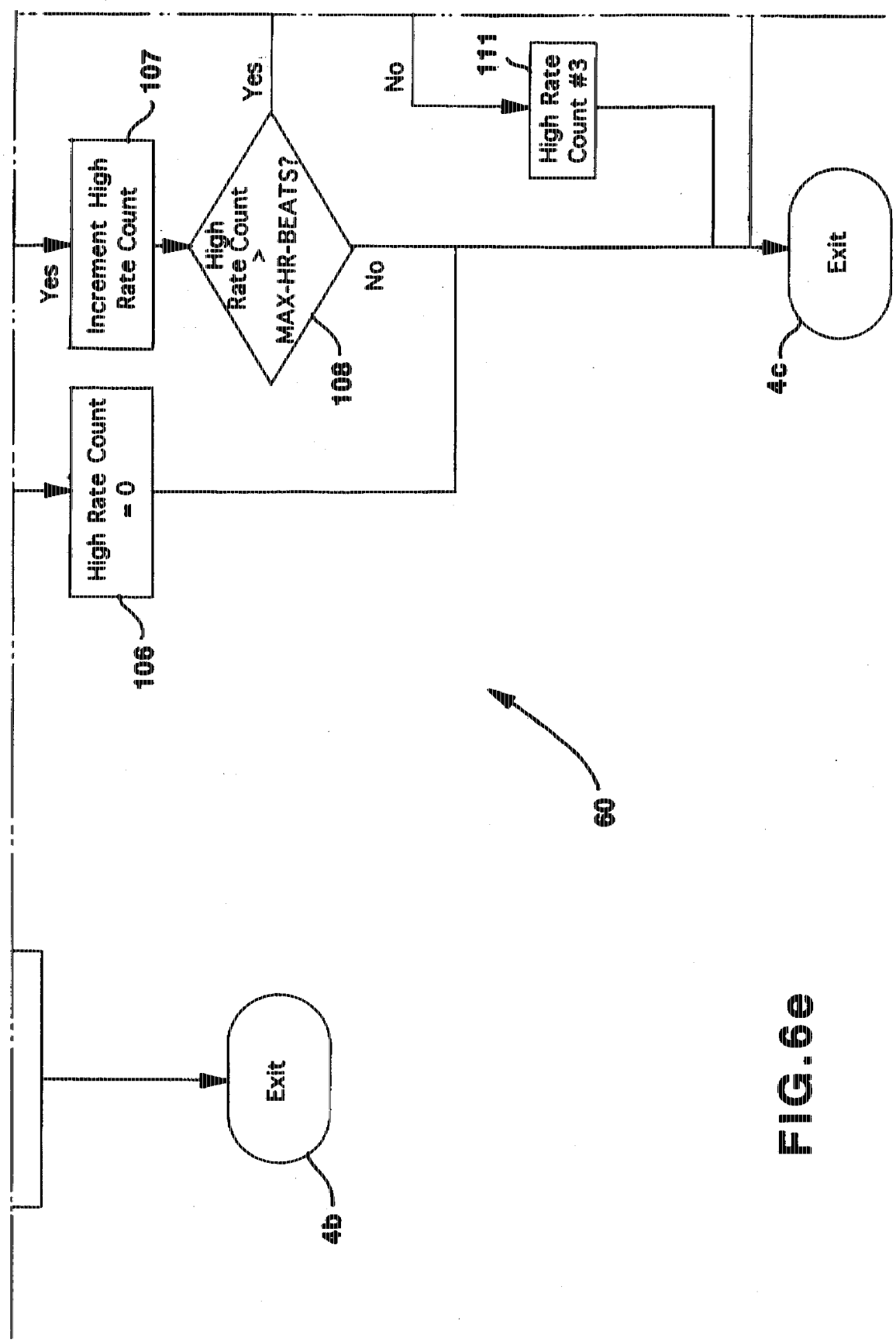
Figure 6F:
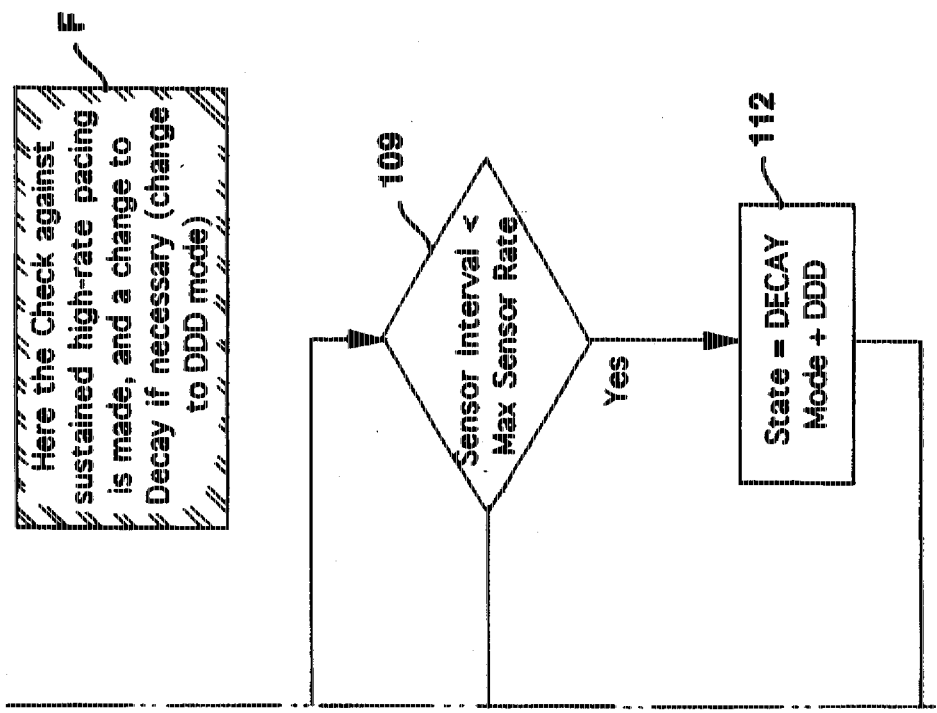

Referring now to FIG. 5 in which a paired flowchart 50a and 50b are illustrated, the beat by beat functioning of an algorithm in accord with a preferred embodiment of this invention is described. If we begin with an atrial pace (51a) then we start with the question, "are we already in a decay state (52a)?", which the program will determine by looking at the memory for this indicator, and if so, then we will increment the decay counter in step 56. In the preferred embodiment of the invention, counters which each are valued at one 8 millisecond increment can be used to both hold the number of decay increments to apply to the pacing pulse timing and to be incremented in accord with the flow chart. Separate counters could be used if desired, and numerous counting methods are readily available to those of ordinary skill. The escape interval in this case of our preferred embodiment will be incremented by eight milliseconds (one increment) when the counter exceeds four, at which time the counter will be reset. (See FIG. 4b-48). The algorithm will then move on to step 57. In step 56 because we are in a "decay" state, in one form of the embodiment the atrial outputs (pulse width, pulse amplitude for stimulation) may also be lowered. (It is known to use autocapture testing algorithms to set the pulse width and duration based on whether pacing is being accomplished at a given level of stimulus, and even to optimize such parameters. It is also believed that once a heart chamber is entrained to a certain pulse value, the energy value of the pacing pulse can be lowered without losing the pacing rate. This algorithm can take advantage of an autocapture feature in a pacemaker if desired to ensure that lowering the energy value (pulse width/amplitude) of the pacing stimulus will not result in loss of capture. By checking for such threshold values before initiation of the consistent pacing algorithm described or during it's execution, the capture of the atrium can be confirmed at a lower value, and on development of a historical relationship of capture to pacing energy value, the size of the drop in pacing energy can be tuned.) We use this four count by 8 millisecond mechanism to provide a smoother or less rapid decay than would occur without such a counter. Other smoothing techniques may be used which are within the ordinary skill of those in this art.

If the program is not already in the decay state, the preferred program asks whether or not the program is in the "delay" state at step 53. If the program is (yes) in this delay state, the algorithm moves to step 55, the delay counter is incremented and "state" is changed to "decay" when the counter exceeds a maximum number of delay beats which we set in the preferred embodiment at 12. This is illustrated in FIG. 4b at 47. Delay operates to provide for a plateaued pacing rate to prevent too rapid switching between decay and "ratchet" or "rise" phases of this program. If the program is not in the "delay" state, the state is changed to "delay" from what we call in this FIG. 5 algorithm a "rise" state and the delay count is reset to zero and the current escape interval value (atrial escape interval) is held. From all of steps 54, 55, and 56 the next step is a determination of the answer to the question is the mechanism pacing within 80 milliseconds of the maximum pace rate (step 57) and if so, (step 58) are there too many consecutive atrial paces too near the maximum pacing rate, and if so, the algorithm moves on to step 65. In other words here in step 55 we decay to an interim rate (43 of FIG. 4a) to wait for intrinsic activity below an intermediate rate and the program then exits that step 53a(1). If at step 57, we find that pacing is not within 80 milliseconds of the maximum pacing rate then we reset a variable called "high rate pace count" at step 59 and again proceed to exit at step 53a(2). (The rise state here is similar to the ratchet state described with reference to FIG. 6.)

If, on the other hand, we are starting at the atrial sense part of the algorithm in step 51b, we move to decrease the escape interval by 40 milliseconds (five basic increments) at 52b and increase the atrial output (pulse width/pulse amplitude) and further change the state of the operation to rise. After this we exit at step 53b.

A similar preferred embodiment algorithm for maintaining a just above the usual atrial pacing rate is described with reference to FIG. 6 as flowchart 60, having explanatory section flag blocks A–C, E, and F.

Flag A indicates that this algorithm in step 13 works with another to determine whether or not the tachy mode switch or other tachy indicator is on in the pacemaker. Flag B describes the program's arm with elements 81–76 which is that segment of the algorithm that provides return to "ratchet" operation. Flag C indicates the area of the algorithm in which the ratcheting back up of the pacing rate occurs upon detection of intrinsic sinus activity. Flag E indicates the segment of the algorithm which is the decay arm, and Flag F indicates the segment used for a check against sustained high rate pacing.

The program 60 starts at input 3. This program can be triggered by automatic diagnostics that are known in the art to suggest the presence of or detect atrial arrhythmias, mode smoothing programs or hysteresis type programs used for automatic responses to sensed atrial arrhythmias, successful arrhythmia termination sequences and so on.

If there is atrial tachycardia present, the algorithm exits at 4a from step 13. If there is not, the algorithm moves to step 19 where it checks its current state. If during initiation a state is not yet set, the program moves to "Ratchet" state.

If the program is in the ratcheting up mode, as determined at block 19, then the last atrial sense will be checked to determine whether it was an atrial pace in block 31 or an atrial refractory sense in block 37. If it is an atrial pace, the increment pace counter, step 33, is taken and a counter value is increased by one and step 35 is next taken. The output of the atrial pulse can be decreased at this step 35 in the preferred embodiment since the atrium is assumed to be entrained. Typical values for entrained atria are around 2V, 0.5 ms compared to typical ratchet values of near 5V, 0.5 ms pulse amplitude, duration.

In the decay state, the first thing the algorithm does is to wait in step 81 for the next atrial sense or paced event. If it is an atrial pace event, then the algorithm moves to step 6 and increments the slow beat counter. If it is a sensed event, then the Pwave to Pwave (P-P) interval is checked to see if it is larger than the resynchronization interval.

By way of explanation if the program moves into the decay phase, it is because of a consistently high sinus rate, causing the program to ratchet up in rate. In decay, the escape interval is increased on each beat (lowering the rate). Thus, the occurrence of atrial pacing means the sinus rate is slower than the rate at which the pacemaker wants to pace (be it sensor rate or some other rate, say a minimum maintenance rate for example).

Also, when P-P intervals are below the resynchronization interval the algorithm gets turned back on (step 76).

Note also that the resynchronization interval is 80 ms (in preferred embodiment) below the maximum rate (41, FIG. 4a).

The next step, step 72 of the program 60, determines by looking at the pace counters set incremented in step 33 whether the pace counter equals the plateau count. If it does, the pace counter is reset to zero and the escape interval is increased by the INC. DELTA amount.

In step 77 the escape interval is set equal to the maximum of the escape interval (its own value) where the lower rate or the sensor rate. If the pace counter however in step 73 is determined to be not equal to the plateau count, then the changes in pace counter and escape interval of step 75 and 77 are not made and the program moves to step 105.

If in step 31 the last atrial event was not an atrial pace, a determination must next be made whether it is an atrial refractory sense (that way it would be an indication that there is ectopy) or in other words that an AT event has occurred. This would also be termed a Premature Atrial Contraction or PAC. If there is no atrial refractory sense (PAC) in step 37 and it had not been an atrial pace in step 31, then the pace counter is reset to zero, (step 101) the escape interval is decreased step is taken in step 102, and the atrial output voltage and or pulse width is set to overdrive value in step 103. The escape interval is then set equal to the minimum of the escape interval or the minimum pace interval in step 104. The sections flagged as C and E thus maintain pacing just above the sinus rate, provided no ectopic beats are found.

Because these two branches (C & E) have a tendency to increase the atrial rate, in step 105 a determination is made of whether or not the escape interval is still producing a rate faster than the high rate cut off over our extended period. If not, then the high rate count is set equal to zero and the ratchet arm of this program is exited at 4C. If the escape interval is higher than the high rate cut off value (80 ms below the maximum rate in the preferred embodiment), the high rate count counter is incremented in step 107 and the high rate count thus incremented is checked in step 108 to determine whether it is now greater than the maximum high rate count level. If it is not, again the program proceeds to exit 4C.

If the high rate count is greater than the maximum high rate allowed in step 108, the preferred embodiment program checks in step 109 whether the sensor interval is still producing a rate faster than the maximum sensor rate. If it is, the high rate count is set back to zero and exit 4C is again taken. We assume in this case the high sinus rate is an appropriate response to exercise. If it is not, however, the state is set to decay and the mode is set for the pacemaker to DDD in step 112. Then the program exits at 4C. If the state has been set to decay on the next go through of flow chart 60 at step 19 the decay branch is taken and it is determined whether or not the last atrial event was an atrial pace in step 81. If it was, the slow beat count is incremented by one. At step 6 and at step 78 a check is made to see if the slow beat count is equal to the resume count. The resume count means that enough beats have occurred at a rate below the resynchronization interval and it is time to reinitialize and restart the algorithm. A larger resume count means there will be less reinitialization starts of the program and a smaller resume count value means the program initiation will be more sensitive.

If the slow beat count is the same as the resume count, then the mode is set to DDI, the state is changed to ratchet, the slow beat count is reset to zero and the total beat count is set to zero in step 76 before the program exits at 4B. If the first decay atrial event is determined at step 81 not to be an atrial pace, a check is made to see if the P wave to P wave interval is greater than the resynchronization interval in step 83. The resynchronization interval is equivalent to the intermediate rate 43 of FIG. 4a which is 80 milliseconds lower than the maximum rate 41. It is also higher than the interim rate 42. The total beats count is kept to prevent high atrial (sinus) rates from thwarting the intent of the program. In other words, a high normal sinus would otherwise disable the program altogether, never allowing the pacer to pace at a rate above the high sinus rate.

In step 85 the total beats count is checked to see if it is greater than the maximum number of decay beats allowed and if it is not, then the total beats count is incremented at step 87 and at step 89 the escape interval is increased by INC DELTA. At step 72 the escape interval is set equal to the maximum of the lower rate and the sensor rate. Basically then, we are looking for either atrial paces (81) which means slow heart rate, or P-P intervals below the Intermediate or Resynchronization rate. When we find them and they add up to a large enough count, we shift to ratchet or rise phase. The program then exits at step 4b.

If these algorithms are applied to ventricular pacing, it could accomplish the same result of reduced arrhythmias in the ventricular chambers. This could be done in a single dual chamber pacemaker. The only modification required for applications to a ventricular pacer is changing every atrial reference to a ventricular reference and references to sinus rate to references to ventricular rate (applying it to VVI/R or DDD/R pacing for example). For dual chamber applications, the idea is the same but the range of possibility is greater, making variants of the algorithms for one or the other chamber, using only one consistent pacing algorithm for either the ventricular or the atria, etc. However it is believed that the use in the atrium alone will also assist with ventricular arrhythmias so long as conduction pathways are normal. An additional element that could be employed in adopting direct consistent ventricular pacing (whether together with an atrial algorithm or not) would be it's application by timing based on decreasing the AV interval rather than basing the timing exclusively on same chamber events, P-P intervals or the like as is described with respect to consistent atrial pacing. With the detailed description of the atrial algorithms described above, application of such AV interval timing for ventricular pulse triggering for a ventricular algorithm is within the ordinary skill of those in this art such that the description in this paragraph is sufficient to apply it to a reader's preferred pacemaker.

More specifically, use of this invention for cases with and without conduction block but with consideration for the ventricular performance beyond mere consistent atrial pacing are as follows.

For conduction block, the ventricle should be paced with a decay mode and a ratchet mode as described above for atrial pacing, but applied to the ventricular pacing control. If there is a ventricular sense, then the control should be passed to the ratchet up part of the inventive algorithm. The ventricular pacing should be maintained until a ventricular sensed event is found, which would indicate and aberrant ventricular action, like a PVC (premature ventricular contraction), suggesting abnormal conduction to the ventricle.

In the case of no conduction block, pacing in both the atrium and ventricle should be made available using both the ratchet and decay parts of the algorithms. In this case there are two options. First, if there are normally conducted ventricular contractions and PVC's (or other aberrant ventricular contractions), the program should be in the ratchet up phase for the atrial rate, driving the ventricular rate up through the consistent atrial pacing. Second option is to ratchet up the atrial rate using the ratchet algorithm and shortening the AV interval to increase the Ventricular rate and ensure paced ventricular contractions. This second option could be used for conduction block patients as well but will obviously require substantially more expenditure of battery power to supply the ventricular pacing.

For both of these applications of course, the suggestion (as with pure consistent atrial pacing, described first, and to the same extent and for the same reasons) to increase the amplitude and/or pulse width of the pacing pulse for the ratchet up mode and to tend to decrease it for the decay mode will apply. Additionally, It is advisable to consider shortening the AV interval during ratchet up and lengthen it during decay modes. These changes can be effectuated by pacing the ventricle before the normal conduction time, or after (assuming no ventricular event is detected)the expected conduction times, in the cases of ratchet up and decay modes, respectively. The advantage of this additional measure is potentially improved hemodynamics and certainly more consistent ventricular pacing. Only one or a combination of all the measures specified in this paragraph may be used as desired or indicated by the patient condition or the design specifications of the device.

Many other minor variations will occur to the reader within the inventive ambit hereof.

We claim:

1. A method for controlling the rate of pacing pulse delivery in an atrium of a heart wherein at least two modes for changing the rate of pacing delivered to said chamber are included in said method, a first of said two modes being a decay mode during which the rate of pacing delivered to the atrium is reduced and a second being a ratchet up mode during which the pacing rate is increased, said method comprising, determining by means of detected atrial events whether there is natural, nonpacemaker induced depolarization or contraction of the atrium, maintaining the pacing rate until it is determined that one such natural atrial event has occurred, switching to a ratchet up mode when natural atrial depolarizations are detected during a period of atrial pacing such that the pacing rate is increased until no further such natural atrial depolarizations or contractions are detected and for a period thereafter maintaining said increased pacing rate, after said period expires, switching to a decay mode until a safety level is reached or a natural atrial depolarization or contraction is detected, if said safety level is reached, continuing to pace at the safety rate, but if natural depolarization or contraction is determined prior to reaching the safety rate in said decay mode, then pacing at an increment above the rate at which the natural depolarization or contraction was found.

2. A method as set forth in claim 1 wherein during the ratchet mode, the pacing output is increased to ensure capture of the atrium by increasing the stimulus energy level of pacing pulses.

3. A method as set forth in claim 1 wherein during the decay mode, the level of the pacing pulse delivered is lowered to conserve power by reducing the stimulus energy level of said pacing pulses.

4. A method as set forth in claim 1 wherein during the decay mode, the level of the pacing pulse delivered is lowered to conserve power by reducing stimulus energy level of said pacing pulses as set by a user.

5. A method as set forth in claim 1 wherein during the decay mode, the level of the pacing pulse delivered is lowered to conserve power by reducing stimulus energy level of said pacing pulses automatically, based on an autocapture threshold driver algorithm.

6. A method as set forth in claim 1 wherein said decay mode lasts until a slow sinus is detected or until a total predetermined maximum decay period has expired.

7. A method as set forth in claim 6 wherein said slow sinus is detected when the heart rate does not exceed a predetermined resynchronization rate.

8. A method as set forth in claim 1 wherein during the decay mode, the level of the pacing pulse delivered is lowered to conserve power by reducing the stimulus energy level automatically.

9. An apparatus for controlling a pacing system for delivering pacing pulses to the atrium of a heart comprising:

Timing control means for controlling the rate of delivery of pacing pulses to said atrium, said timing control means capable of at least two modes of adjustment, one of said at least two being a decay mode and the other of said at least two being a ratchet up mode, atrial contraction sense means for detecting atrial events and producing a signal therefrom, and for distinguishing between natural and induced contractions or depolarizations, switching means for signaling said timing control means to change to a ratchet up mode when natural atrial depolarizations are detected such that the pacing rate is increased until no further such natural atrial contractions are detected and for a period thereafter maintaining said increased pacing rate, and after said period expires, switching to a decay mode until either a safety pacing rate level is reached or a natural atrial contraction is detected, if said safety level is reached, continuing to pace at the safety rate, but if natural atrial contraction is detected prior to reaching the safety rate in said decay mode, then signaling said timing control means to pace at a rate greater by an increment than a rate at which the natural depolarization or contraction was found.

10. Apparatus as set forth in claim 9 wherein during the ratchet mode, the stimulus energy level of pacing pulses is increased by a rise state program to ensure capture of the atrium.

11. Apparatus as set forth in claim 9 wherein during the decay mode, the level of the pacing pulse delivered is lowered by a decay state program to conserve power by reducing the stimulus energy level.

12. Apparatus as set forth in claim 9 wherein a user operating a programmer to modify a rise state and a decay state program may set the level of the pacing pulse stimulus energy level.

13. Apparatus as set forth in claim 9 further comprising a capture detection processor having an algorithm for determining and setting amplitude and/or pulse width of pacing pulses delivered automatically, and further comprising means to lower the stimulus energy level during the decay mode from said determined level to conserve power operative during the decay mode.

14. Apparatus as set forth in claim 9 wherein said decay mode is constructed to terminate when a slow sinus is detected or when a total predetermined maximum decay period has expired, whichever occurs first.

15. Apparatus as set forth in claim 14 wherein a slow sinus detection means having a comparitor detects a slow sinus by comparing the heart rate and a predetermined resynchronization rate when said comparitor finds that the heart rate does not exceed said predetermined resynchronization rate.

16. A method for controlling the rate of pacing pulse delivery in a heart so as wherein at least two modes for changing the rate of pacing delivered to a ventricle are included in said method, a first of said two modes being a decay mode during which the rate of pacing delivered to the ventricle is reduced and a second being a ratchet up mode during which the pacing rate to the ventricle is increased, said method comprising, determining by means of detected ventricular events whether there is natural, nonpacemaker induced depolarization or contraction of the ventricle, maintaining the pacing rate until it is determined that one such natural ventricular event has occurred, switching to a ratchet up mode when natural ventricular depolarizations are detected during a period of ventricular pacing such that the pacing rate is increased until no further such natural depolarizations or contractions are detected and for a period thereafter maintaining said increased pacing rate, after said period expires, switching to a decay mode until a safety level is reached or a natural ventricular depolarization or contraction is detected, if said safety level is reached, continuing to pace at the safety rate, but if natural depolarization or contraction is determined prior to reaching the safety rate in said decay mode, then pacing at an increment above the rate at which the natural depolarization or contraction was found.

17. A method as set forth in claim 16 wherein during the ratchet mode, the pacing output is increased to ensure capture of the ventricle by increasing the stimulus energy level of ventricular pacing pulses.

18. A method as set forth in claim 16 wherein during the decay mode, the level of the pacing pulse delivered is lowered to conserve power by reducing the stimulus energy level.

19. A method as set forth in claim 16 wherein during the decay mode, the level of the pacing pulse delivered is lowered to conserve power by reducing the stimulus energy level as set by a user.

20. A method as set forth in claim 16 wherein during the decay mode, the level of the pacing pulse delivered is lowered to conserve power by reducing the stimulus energy level automatically, based on an autocapture threshold driver algorithm.

21. A method as set forth in claim 16 wherein said decay mode lasts until a slow sinus is detected or until a total predetermined maximum decay period has expired.

22. A method as set forth in claim 21 wherein said slow sinus is detected when the heart rate does not exceed a predetermined resynchronization rate.

23. An apparatus for controlling a pacing system for delivering pacing pulses to a ventricle of a heart comprising:

Timing control means for controlling the rate of delivery of pacing pulses to said atrium, said timing means capable of at least two modes of adjustment, one of said at least two being a decay mode and the other of said at least two being a ratchet up mode, ventricular contraction sense means for detecting ventricular events and producing a signal therefrom, and for distinguishing between natural and induced contractions or depolarizations of a ventricle, switching means for signaling said timing control means to change to a ratchet up mode when natural ventricular depolarizations are detected such that the pacing rate is increased until no further such natural ventricular contractions are detected and for a period thereafter maintaining said increased pacing rate, and after said period expires, switching to a decay mode until either a safety pacing rate level is reached or a natural ventricular contraction is detected, if said safety level is reached, continuing to pace at the safety rate, but if natural ventricular contraction is detected prior to reaching the safety rate in said decay mode, then signaling said timing control means to pace at a rate greater by an increment than a rate at which the natural depolarization or contraction was found.

24. Apparatus as set forth in claim 23 wherein during the ratchet mode, the stimulus energy level of pacing pulses is increased by a rise state program to ensure capture of the ventricle.

25. Apparatus as set forth in claim 23 wherein during the decay mode, the level of the pacing pulse delivered is lowered by a decay state program to conserve power by reducing the stimulus energy level.

26. Apparatus as set forth in claim 23 wherein a user operating a programmer to modify a rise state and a decay state program may set the level of the pacing pulse stimulus energy level.

27. Apparatus as set forth in claim 23 further comprising a capture detection processor having an algorithm for determining and setting the stimulus energy level of pacing pulses delivered automatically, and further comprising means to lower the stimulus energy level during the decay mode from said determined level to conserve power operative during the decay mode.

28. Apparatus as set forth in claim 23 wherein said decay mode is constructed to terminate when a slow sinus is detected or when a total predetermined maximum decay period has expired, whichever occurs first.

29. Apparatus as set forth in claim 28 wherein a slow sinus detection means having a comparitor detects a slow sinus by comparing the heart rate and a predetermined resynchronization rate when said comparitor finds that the heart rate does not exceed said predetermined resynchronization rate.

30. A method for controlling the rate of pacing pulse delivery in a ventricle and an atrium of a heart wherein at least two modes for changing the rate of pacing delivered to a ventricle are included in said method, a first of said two modes being a decay mode during which the rate of pacing delivered to the ventricle is reduced and a second being a ratchet up mode during which the pacing rate to the ventricle is increased, said method comprising, determining by means of detected ventricular events whether there is natural, nonpacemaker induced depolarization or contraction of the ventricle, maintaining the pacing rate until it is determined that one such natural ventricular event has occurred, switching to a ratchet up mode when natural non-paced ventricular depolarizations are detected during a period of atrial pacing such that the pacing rate is increased until no further such natural depolarizations or contractions are detected and for a period thereafter maintaining said increased pacing rate, after said period expires, switching to a decay mode until a safety level is reached or a natural nonpacemaker induced depolarization or contraction is detected, if said safety level is reached, continuing to pace at the safety rate, but if nonpacemaker induced depolarization or contraction is detected prior to reaching the safety rate in said decay mode, then pacing at an increment above the rate at which the natural depolarization or contraction was found.

31. A method as set forth in claim 30 wherein during the ratchet mode, the pacing output is increased to ensure capture of the ventricle by increasing the stimulus energy level of pacing pulses.

32. A method as set forth in claim 30 wherein during the decay mode, the level of the pacing pulse delivered is lowered to conserve power by reducing the stimulus energy level.

33. A method as set forth in claim 30 wherein during the decay mode, the level of the pacing pulse delivered is lowered to conserve power by reducing the stimulus energy level as set by a user.

34. A method as set forth in claim 30 wherein during the decay mode, the level of the pacing pulse delivered is lowered to conserve power by reducing stimulus energy level automatically, based on an autocapture threshold driver algorithm.

35. A method as set forth in claim 30 wherein said decay mode lasts until a slow sinus is detected or until a total predetermined maximum decay period has expired.

36. A method as set forth in claim 35 wherein said slow sinus is detected when the heart rate does not exceed a predetermined resynchronization rate.

37. A method as set forth in claim 30 wherein during the decay mode, lengthen the AV interval.

38. A method as set forth in claim 30 wherein during the ratchet up mode, shorten the AV interval.

39. An apparatus for controlling a pacing system for delivering pacing pulses to an atrium and a ventricle of a heart comprising:

Timing control means for controlling the rate of delivery of pacing pulses to said atrium, said timing means capable of at least two modes of adjustment, one of said at least two being a decay mode and the other of said at least two being a ratchet up mode, ventricular contraction sense means for detecting ventricular events, and for distinguishing between natural non-pace induced and induced contractions or depolarizations of a ventricle, switching means for signaling said timing control means to change to a ratchet up mode when natural ventricular depolarizations are detected such that the pacing rate is increased until no further such natural ventricular contractions are detected and for a period thereafter maintaining said increased pacing rate, and after said period expires, switching to a decay mode until either a safety pacing rate level is reached or a natural ventricular contraction is detected, if said safety level is reached, continuing to pace at the safety rate, but if natural ventricular contraction is detected prior to reaching the safety rate in said decay mode, then signaling said timing control means to pace at a rate greater by an increment than a rate at which the natural non-pace induced ventricular depolarization or contraction was found.

40. Apparatus as set forth in claim 39 wherein during the ratchet mode, the stimulus energy level of pacing pulses is increased to ensure capture of the ventricle.

41. Apparatus as set forth in claim 39 wherein during the decay mode, the level of the pacing pulse delivered is lowered to conserve power by reducing stimulus energy level.

42. Apparatus as set forth in claim 39 wherein a user may set the level of the pacing pulse stimulus energy level.

43. Apparatus as set forth in claim 39 further comprising a capture detection processor having an algorithm for determining and setting the stimulus energy level of pacing pulses delivered automatically, and further comprising means to lower the stimulus energy level during the decay mode from said determined level to conserve power operative during the decay mode.

44. Apparatus as set forth in claim 39 wherein said decay mode is constructed to terminate when a slow sinus is detected or when a total predetermined maximum decay period has expired, whichever occurs first.

45. Apparatus as set forth in claim 44 wherein a slow sinus detection means having a comparitor detects a slow sinus by comparing the heart rate and a predetermined resynchronization rate when said comparator finds that the heart rate does not exceed said predetermined resynchronization rate.

46. Apparatus as set forth in claim 39 wherein during the decay mode, said switching means sends a signal to said control means to lengthen the AV interval.

47. Apparatus as set forth in claim 39 wherein during the ratchet up mode, said switching means sends a signal to said control means to shorten the AV interval.

* * * * *